United States Patent [19]

Fujita et al.

[11] Patent Number: 4,539,086
[45] Date of Patent: Sep. 3, 1985

[54] OXYGEN CONCENTRATION CONTROLLING METHOD AND SYSTEM

[75] Inventors: Yuko Fujita; Hisashi Kudo, both of Kyoto, Japan

[73] Assignee: Japan Storage Battery Company Limited, Kyoto, Japan

[21] Appl. No.: 612,945

[22] Filed: May 23, 1984

[30] Foreign Application Priority Data

Aug. 31, 1983 [JP] Japan .................................. 58-160075
Aug. 31, 1983 [JP] Japan .................................. 58-160076
Sep. 17, 1983 [JP] Japan .................................. 58-171920

[51] Int. Cl.³ .......................... C25B 1/02; C25B 9/00
[52] U.S. Cl. ................................. 204/129; 204/130;
204/263; 204/265; 204/266; 204/283; 204/1 T;
204/427
[58] Field of Search ........ 204/129, 130, 263, 265–266,
204/283, 1 T, 195 R

[56] References Cited

U.S. PATENT DOCUMENTS 3,410,770 11/1968 Buechler .............................. 204/129
3,410,783 11/1968 Tomter .................................. 204/129
3,755,128 8/1973 Herwig .................................. 204/129
4,105,523 8/1978 Stolarezyk .......................... 204/129

OTHER PUBLICATIONS

"Electrolytic Sep. & Purif. of $O_2$ from a Gas Mix." by S. H. Langer et al., J. Phy. Chem., vol. 68, #4, Apr. 1964, pp. 962–963.

Primary Examiner—R. L. Andrews
Attorney, Agent, or Firm—Sughrue, Mion, Zinn, Macpeak, and Seas

[57] ABSTRACT

In the invention, an electrochemical cell including an oxygen reducing cathode, an oxygen generating anode and an electrolyte, and having both a deoxygenating function and an oxygen generating function is coupled to a chamber in such a manner that, when the oxygen concentration in the chamber is much higher than a predetermined value, the deoxygenating function is utilized to decrease the oxygen concentration and when the oxygen concentration in the chamber is much lower than the predetermined value, the oxygen generating function is utilized to increase the oxygen concentration so that the oxygen concentration in the chamber is maintained at the predetermined value.

16 Claims, 4 Drawing Figures

OXYGEN CONCENTRATION CONTROLLING METHOD AND SYSTEM

BACKGROUND OF THE INVENTION

1. Technical Field

This invention relates to a method of controlling the oxygen concentration of a mixture gas containing oxygen, and a system for practicing the method, and more particularly to an oxygen concentration controlling method in which electrochemical means is utilized to automatically control the oxygen concentration in a chamber or the like to a desired value, and to a system for practicing the method.

In scientific experiments such as biological, medical, metallurgical and chemical experiments, it is often required to control the oxygen concentration of an atmosphere to a desired value. For instance, in cultivating cells, the rate of cultivation is closely related to the oxygen concentration. Thus, there has been a strong demand for the provision of a simple method of controlling oxygen concentration.

2. Prior Art

Heretofore, in order to control the oxygen concentration in a chamber, a mixture gas was prepared by mixing oxygen with an inert gas such as nitrogen, argon or helium, or with carbon dioxide until a desired oxygen concentration was obtained, and was supplied into the chamber. In another conventional method, when the oxygen concentration in the chamber was much higher than a predetermined value, inert gas was supplied into the chamber, and when the oxygen concentration was much lower than the predetermined value, oxygen gas was supplied thereinto. However, these conventional methods are disadvantageous in that the gas cylinder operation and gas flow control are troublesome, and the gas used for control is expensive.

SUMMARY OF THE INVENTION

In an oxygen concentration controlling method, an electrochemical cell including an oxygen reducing cathode, an oxygen generating anode and an electrolyte, and having both a deoxygenating function and an oxygen generating function, is coupled to a chamber in such a manner that, when the oxygen concentration in the chamber is much higher than a predetermined value, the deoxygenating function is utilized to decrease the oxygen concentration conversely, when the oxygen concentration in the chamber is much lower than the predetermined value, the oxygen generating function is utilized to increase the oxygen concentration so that the oxygen concentration in the chamber is maintained at the predetermined value.

DETAILED DESCRIPTION OF THE PREFERRED EMBODIMENTS

Figure 1:
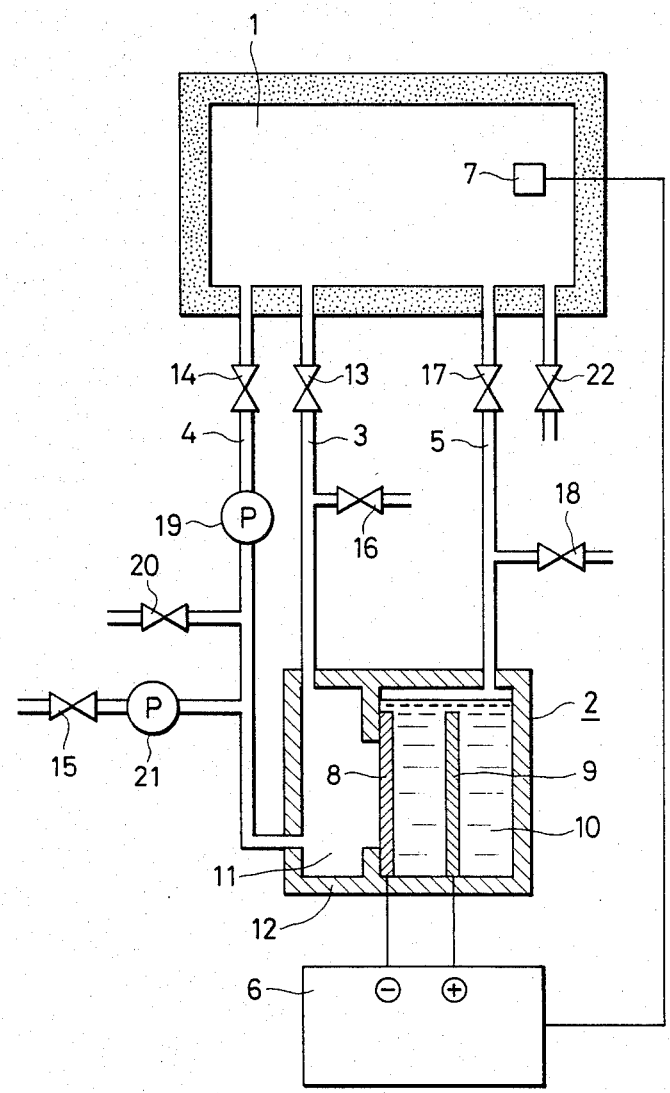
FIGS. 1 through 4 are explanatory diagram showing first through fourth examples of an oxygen concentration controlling system according to this invention, respectively.

The Journal of Physical Chemistry, vol. 68(4), pp 962 to 963 (1964) and U.S. Pat. No. 3,489,670 (Jan. 31, 1970) disclose a method in which electrochemical means is used to separate oxygen from a mixture gas and to purify the same. The method is based on the following principle: When, in an electromechanical cell having a cathode comprising a gas diffusion electrode effective in oxygen electrolytic reduction, an anode comprising an inactive electrode and an electrolyte of potassium hydroxide or sodium hydroxide solution or an ion exchange membrane, a DC voltage is applied between the anode and cathode while a mixture gas such as air containing oxygen is supplied to the cathode, oxygen is selectively consumed at the cathode by the following reaction:

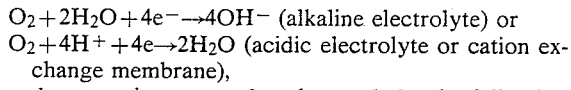

and oxygen is generated at the anode by the following reaction:

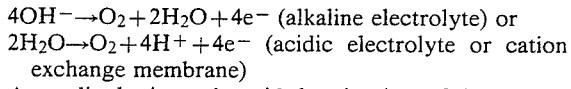

Accordingly, it can be said that, in view of the oxygen generated at the anode, the electrochemical cell serves as an oxygen generator, an oxygen purifier or an oxygen concentrator.

However, the utilization of electrochemical reaction has not been heretofore proposed nor suggested to control an oxygen concentration.

A first object of this invention is to provide a novel and unique oxygen concentration controlling method in which the electrochemical cell is allowed to have both an oxygen generating function and a deoxygenating function the latter wing the above-described deoxygenating reaction at the cathode.

A second object of the invention is to provide an oxygen concentration controlling system in which electrochemical means is used to effectively control the oxygen concentration in a chamber.

A third object of the invention is to provide an oxygen concentration controlling system usuable with a cell cultivating device.

A fourth object of the invention is to provide an electrochemical cell which is especially effective especially when a cation exchange membrane is employed as the electrolyte.

In a typical example of the oxygen concentration controlling system according to the invention, a chamber, the oxygen concentration in which is to be controlled, is connected to an electrochemical cell having both a deoxygenating function and an oxygen generating function. More specifically, in the electrochemical cell, a cathode gas chamber is provided behind the cathode, and an oxygen lead-out section is provided on the anode side, so that the chamber is coupled to the electrochemical cell through a gas path including the cathode gas chamber and a gas path including the oxygen lead-out section. The gas path including the cathode gas chamber is a deoxygenating path, and the gas path including the oxygen lead-out section is an oxygen supplying path. The deoxygenating path comprises a deoxygenating supply path and deoxygenating return path. The deoxygenating path is provided with a circulating pump and an air lead-in pump.

A deoxygenated residual gas purge valve is provided in the deoxygenating supply path, while an air lead-in valve for negative pressure compensation is provided in the deoxygenating return path. An oxygen purge valve is provided in the oxygen supplying path. An overpressure compensating valve is provided for the chamber, or is provided in the deoxygenating return path.

An oxygen sensor is provided in the chamber or in the deoxygenating return path. A power control section is connected to the electrochemical cell.

When, in the oxygen concentration controlling system thus configured, the oxygen sensor indicates that the oxygen concentration in the chamber is much higher than a predetermined value, the electrochemical cell functions as deoxygenating means. In other words, the circulating pump in the deoxygenating path is driven so that the gas in the chamber is supplied into the cathode gas chamber, while a DC voltage is applied between the anode and cathode in the electrochemical cell. As a result, deoxygenation takes place at the cathode, and the deoxygenated residual gas is supplied into the chamber. In this operation, the deoxygenated residual gas purge valve is kept closed. On the other hand, oxygen generated at the anode is not supplied into the chamber, being purged through the oxygen purge valve. The deoxygenation process lowers the pressure in the system including the chamber and the deoxygenating path to less than atmospheric pressure. Therefore, ambient air is introduced into the system through the air lead-in valve until the pressure reaches the atmospheric level. The air thus introduced is also deoxygenated at the cathode. Thus, the oxygen concentration in the chamber is decreased to the predetermined value.

When, on the other hand, the oxygen concentration in the chamber is lower than the predetermined value, the electrochemical cell functions as oxygen generating means. In this case, instead of the circulating pump, an air lead-in pump is driven so that ambient air is supplied to the cathode gas chamber, while a DC voltage is applied between the anode and cathode in the electrochemical cell, so that oxygen generated at the anode is supplied into the chamber. In this operation, the deoxygenated residual gas is not supplied into the chamber, being purged out of the system through the deoxygenated residual gas purge valve, and the oxygen purge valve is kept closed.

As the oxygen is supplied into the chamber, the pressure in the chamber becomes higher than atmospheric. In this case, the gas in the chamber is purged through the overpressure compensating valve until the pressure in the chamber becomes equal to atmospheric pressure.

The oxygen concentration in the chamber is increased to the predetermined value as described above, and the oxygen concentration control is automatically performed in response to instructions from the power control section.

The chamber may be coupled to the electrochemical cell through pipes; however, it is also effective to couple the chamber to the electrochemical cell through detachable fluid couplings each consisting of a plug and a socket with a sleeve. When the latter method is employed, one oxygen concentration controlling device can readily control the oxygen concentrations in a plurality of chambers. Therefore, the present method is especially advantageous when oxygen concentration in each of several chambers are to be kept at different levels.

In addition, a method in which a plurality of small boxes are accommodated in the chamber and the oxygen concentrations in the small boxes are sequentially controlled is useful due to the following reason: The deoxygenating rate and the oxygen generating rate of an electrochemical cell are proportional to the amount of current flowing through the electrochemical cell, and the amount of current is limited by the working area of the electrode of the electrochemical cell. Therefore, as the volume of gas in the chamber is decreased, the capacity of the electrochemical cell can be decreased, and its manufacturing cost can be reduced as much.

A cell cultivating device is generally operated at a temperature of 37° C. and at a relative humidity of 100%. On the other hand, in the case where the electrolyte in the electrochemical cell is an acid solution or a cation exchange membrane, water is formed at the cathode. This water should be removed to permit the cathode to operate satisfactorily. However, it is rather difficult to remove the water when the relative humidity of the gas supplied to the cathode is 100%.

This difficulty may be effectively eliminated by the following methods: In the first method, gas having a relative humidity of 100% coming out of the chamber is heated so that gas of lower relative humidity is supplied to the cathode gas chamber. In the second method, as was described before, in the deoxygenating path, without gas circulation, ambient air is supplied to the cathode gas chamber, so that the residual gas deoxygenated at the cathode is supplied into the chamber and the gas expelled from the chamber is purged out of the system.

The cathode of the electrochemical cell is of the same design as that of a fuel cell. For instance, in the case where the electrolyte is an alkaline solution, a three-layer electrode can be used which is made up of a first layer, namely, a porous nickel sheet, a second layer, namely, a platinum catalysed carbon and polytetrafluoroethylene mixture layer, and a third layer, namely, a porous polytetrafuoroethylene film. In the case where the electrolyte is an acidic solution such as sulfuric acid, an electrode is used which consists of a gold-plated expanded titanium core, a catalyst layer of a platinum catalysed carbon and polytetrafluoroethylene mixture and a backing layer of porous polytetrafluoroethylene. In the case where the electrolyte is a cation exchange membrane which is prepared by applying sulfonic acid radical to perfluorocarbon, the cathode is manufactured according to a method in which a mixture of a platinum group metal and polytetrafluoroethylene is hot-pressed on a cation exchange membrane. However, the cathode manufactured according to this method is disadvantageous in that, as the cathode reaction takes place only at the two-dimensional interface between the cation exchange membrane and the cathode, the reaction speed is low. This problem has been eliminated in the invention. That is, in the invention, powder obtained by adding sulfonic acid radical to cation exchange resin polymer powder such as stylene divinyl benzene copolymer or perfluorocarbon is mixed in the cathode. In the cathode, a number of three-dimensional contacts are formed between the cathode catalyst and the solid electrolyte, to accelerate the cathode reaction.

When the electrolyte is an alkaline solution, the material of the anode may be nickel. When the electrolyte is an acidic solution, the anode material may be gold-plated titanium. When the electrolyte is a cation exchange membrane, the anode material may be iridium oxide or a platinum group metal. In the case where a cation exchange membrane is used as the electrolyte, a platinum group metal is integrally bonded to a cation exchange membrane by electroless plating, or a mixture of platinum group metal or iridium oxide powder and fluororesin binder such as polytetrafluoroethylene is hot-pressed on the cation exchange membrane.

Now, the invention will be described in detail with reference to its preferred embodiments.

First Embodiment

FIG. 1 is a diagram showing an oxygen concentration controlling system according to a first embodiment of the invention.

As shown in FIG. 1, a chamber 1 is communicated through a deoxygenating supply path 3, a deoxygenating return path 4 and an oxygen supplying path 5 to an electrochemical cell 2. The electrochemical cell 2 is coupled to a power control section 6, which is connected to an oxygen sensor 7 provided in the chamber 1.

The electrochemical cell 2 comprises: an oxygen reducing cathode 8 which is a gas diffusion electrode; an anode 9 which is an oxygen generating electrode fabricated of platinum-plated titanium sheet; an electrolyte 10 which is a sulfuric acid solution of 2.5 mol/l; a cathode gas chamber 11; and a cell frame 12.

When the oxygen concentration in the chamber 1 detected by the oxygen sensor 7 is much higher than a predetermined value, then a deoxygenating supply path valve 13 in the deoxygenating supply path 3 and a deoxygenating return path valve 14 in the deoxygenating return path 4 are opened, an air lead-in valve 15 and a deoxygenated residual gas purge valve 16 are closed, an oxygen supply valve 17 in the oxygen supplying path 5 is closed, and an oxygen purge valve 18 is opened.

Under this condition, a circulating pump 19 is driven to cause the gas in the chamber to circulate through the deoxygenating return path 4, the cathode gas chamber 11 and the deoxygenating supply path 3 in the stated order, while DC current is applied between the electrodes 8 and 9 by the power control section 6. As a result, the oxygen concentration in the chamber 1 is decreased to the predetermined value. Oxygen generated from the anode 9 is discarded through the oxygen purge valve 18.

The deoxygenation process lowers the pressure in the system consisting of the chamber 1, the deoxygenating supply path 3, the deoxygenating return path 4 and the cathode gas chamber 11 to less than the atmospheric level. This phenomenon is compensated for by a negative pressure compensating valve 20. More specifically, when the pressure in the system becomes lower than atmospheric, the valve 20 is opened, so that ambient air is introduced into the deoxygenating return path 4. Thus, atmospheric pressure is maintained in the system at all times. The oxygen in the ambient air thus introduced through the compensating valve is also consumed at the cathode 8.

When the oxygen concentration in the chamber 1 is much lower than the predetermined valve, both the deoxygenating supply path valve 13 in the deoxygenating supply path 3 and the deoxygenating return path valve 14 in the deoxygenating return path 4 are closed, the air lead-in valve 15 and the deoxygenated residual gas purge valve 16 are opened, the oxygen supply valve 17 in the oxygen supply path 5 is opened, and the oxygen purge valve 18 is closed.

Under this condition, an air lead-in pump 21 is driven to supply ambient air into the cathode gas chamber 11, while DC current is applied between the cathode 8 and the anode 9, so that oxygen generated from the anode 9 is supplied into the chamber 1 until the predetermined oxygen concentration is obtained. The residual gas deoxygenated at the cathode 8 is purged out of the system through the purge valve 16.

When the supply of oxygen increases the pressure in the chamber 1, an overpressure compensating valve 22 is opened so that the pressure in the chamber 1 becomes equal to atmospheric.

The above-described valve operations are automatically carried out.

When, in the above-described oxygen concentration controlling system, the internal volume of the chamber 1 was 30 l and the working area of the cathode 8 and anode 9 was 4 dm$^2$ respectively, it took 45 minutes to change the oxygen concentration in the chamber 1 from 21% to 10%, and 30 minutes from 21% to 30%.

Second Embodiment

Figure 2:
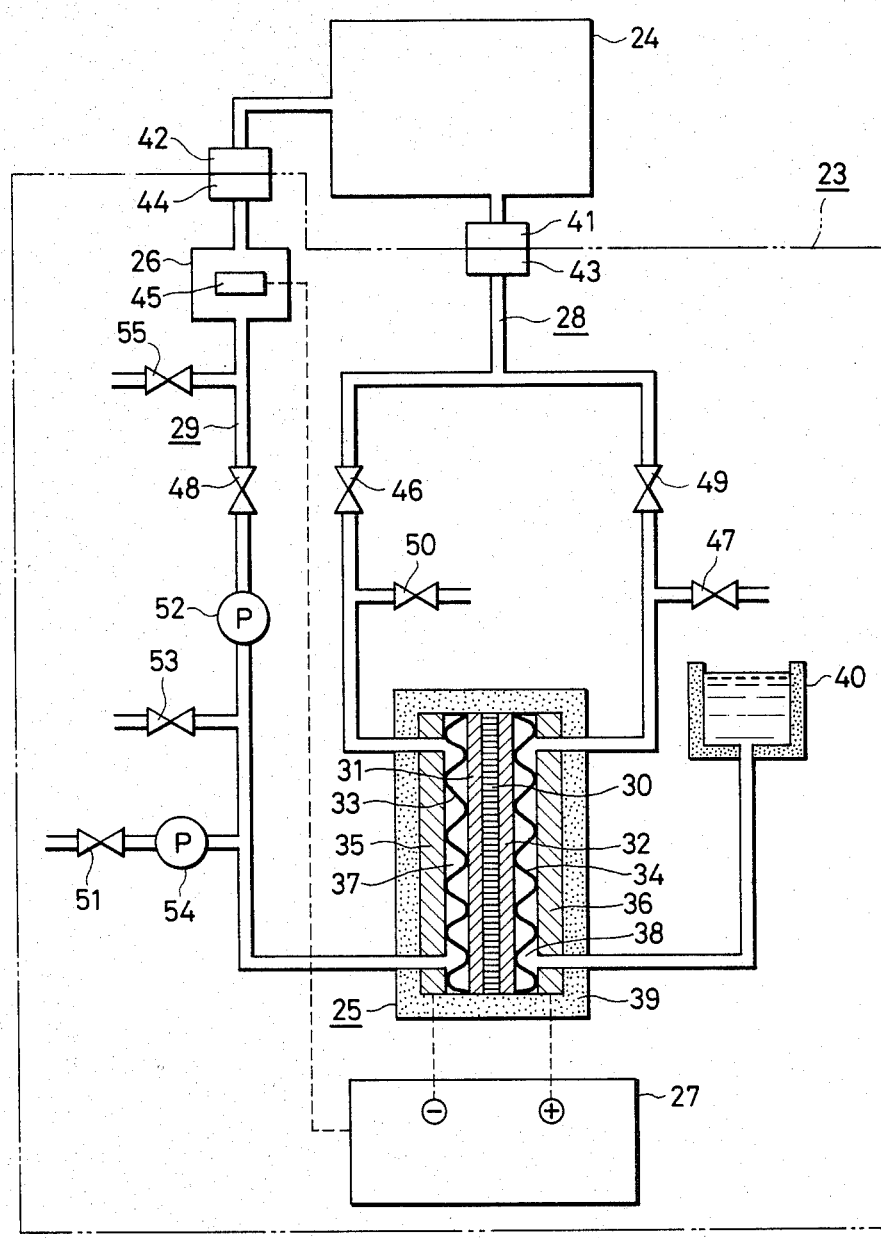

FIG. 2 is an explanatory diagram showing an oxygen concentration controlling system according to the second embodiment of the invention.

Roughly stated, the oxygen concentration controlling system comprises an oxygen concentration control device 23 and a chamber 24. The oxygen concentration control device 23 includes an electrochemical cell 25, an oxygen concentration detecting chamber 26, an electrical control section 27 for controlling oxygen concentration, a gas supply path 28 and a gas return path 29.

The electrochemical cell 25 comprises: a cation exchange membrane 30 prepared by applying sulfonic acid radical to perfluorocarbon; a cathode 31 made of a mixture of platinum black powder and polytetrafluoroethylene; an anode 32 made of a mixture of iridium oxide and polytetrafluoroethylene; a cathode current collector 33 of platinum-plated expanded titanium; an anode current collector 34 of platinum-plated expanded titanium; a cathode terminal plate 35 made of a titanium plate; an anode terminal plate 36 made of a titanium plate; a cathode gas chamber 37; an anode water chamber 38; and a cell frame 39.

The cathode 31 and the anode 32 are bonded to the cation exchange membrane 30. Water is supplied into the anode water chamber 30 from a water tank 40, so that the cation exchange membrane 30 acts as a hydrogen ion conductor.

A supply path gas plug 41 and a return path gas plug 42 are detachably connected to the chamber 24. A supply path gas socket 43 is connected to one end of the gas supply path 28 in the oxygen concentration control device 23, and a return path gas socket 44 is connected to one end of the gas return path 29. The plug 41 is connected to the socket 43, and the return path gas plug 42 is connected to the return path gas socket 44, so that the oxygen concentration control device 23 is communicated with the chamber 24. When the gas plugs are disconnected from the gas sockets, the gas plugs serve as valves to keep the chamber gastight.

The oxygen concentration in the chamber 24 is detected by an oxygen sensor 45 in the oxygen concentration detecting chamber 26. The output signal of the oxygen sensor 45 is supplied to the electrical control section 27.

When the oxygen concentration in the chamber 24 is much higher than a required value, the electrochemical cell 25 operates for deoxygenation. That is, a supply path deoxygenating gas valve 46 in the path 28 and a return path deoxygenating gas valve 48 in the gas return path 29 are opened, an oxygen supply valve 49 and a deoxygenated residual gas purge valve 50 in the path 28 are closed, and an air lead-in valve 51 in the gas return path 29 is closed. Under this condition, a circulating pump 52 is driven, while DC current is applied between the cathode terminal plate 35 and the anode terminal plate 36. As a result, the gas in the chamber 24 is supplied through the gas return path 29 to the cathode gas chamber 37, so that a deoxygenation reaction occurs at the cathode 31 and the deoxygenated gas is supplied through the deoxygenating gas valve 46 to the chamber 24. In the deoxygenation reaction, oxygen generated from the anode 32 is purged out of the system through an oxygen purge valve 47.

A negative pressure compensating valve 53 is provided in the gas return path 29. The valve 53 is made up of a so-called "relief valve", or a liquid valve using a liquid such as propylene glycol of low vapor pressure. When the pressure in the system is reduced by deoxygenation, the valve 53 is used to compensate for the negative pressure by automatically introducing air into the system. The oxygen in the air introduced for the negative pressure compensation is also removed by the electrochemical cell 25.

The above-described gas circulation and deoxygenation operations are repeatedly carried out until the oxygen concentration in the chamber 24 is reduced to the required value.

When the oxygen concentration in the chamber 24 is much lower than a required value, the electrochemical cell 25 operates as an oxygen generating means. In this case, the deoxygenated residual gas purge valve 50 and an air lead-in valve 51 are opened, and the supply path deoxygenating gas valve 46, the oxygen purge valve 47 and the return path deoxygenating gas valve 48 are closed. Under this condition, DC current is applied between the cathode terminal plate 35 and the anode terminal plate 36 while an air lead-in pump 54 is driven. As a result, ambient air outside the system is supplied into the cathode gas chamber 37 by the pump 54, so that an oxygen electrolytic reduction occurs at the cathode 31. The deoxygenated gas is purged out of the system through the deoxygenated residual gas purge valve 50, while oxygen generated from the anode 32 is supplied into the chamber 24 through the oxygen supply valve 49. The gas expelled from the chamber 24 is purged out of the system through the oxygen concentration detecting chamber 26 and an overpressure compensating valve 55 in the gas return path 29. When the oxygen sensor 45 in the oxygen concentration detecting chamber 26 indicates the required value, the application of DC current is suspended.

The above-described various valves except for the negative pressure compensating valve 53 and the overpressure compensating valve 55 are electromagnetic valves which are operated (opened and closed) automatically in a suitable order by a sequencing circuit in the electrical control section 27. The circulating pump 52 and the air lead-in pump 54 are also operated according to a predetermined sequence.

After the oxygen concentration in the chamber 24 has reached the required value, the gas socket 43 is disconnected from the gas plug 41, and the return path gas socket 44 is disconnected from the return path gas plug 42, so that the chamber 24 is disconnected from the oxygen concentration control device 23. In order to maintain the temperature of the chamber 24 unchanged, the chamber 24 should be kept thermostatic.

In the case where the working area of the cathode 31 and anode 32 in the electrochemical cell 25 was 2 dm$^2$ respectively, and the internal volume of the chamber 24 was 15 l, and there was air in the chamber 24, the oxygen concentration could be changed to 10% or 30% in twenty minutes.

Third Embodiment

Figure 3:
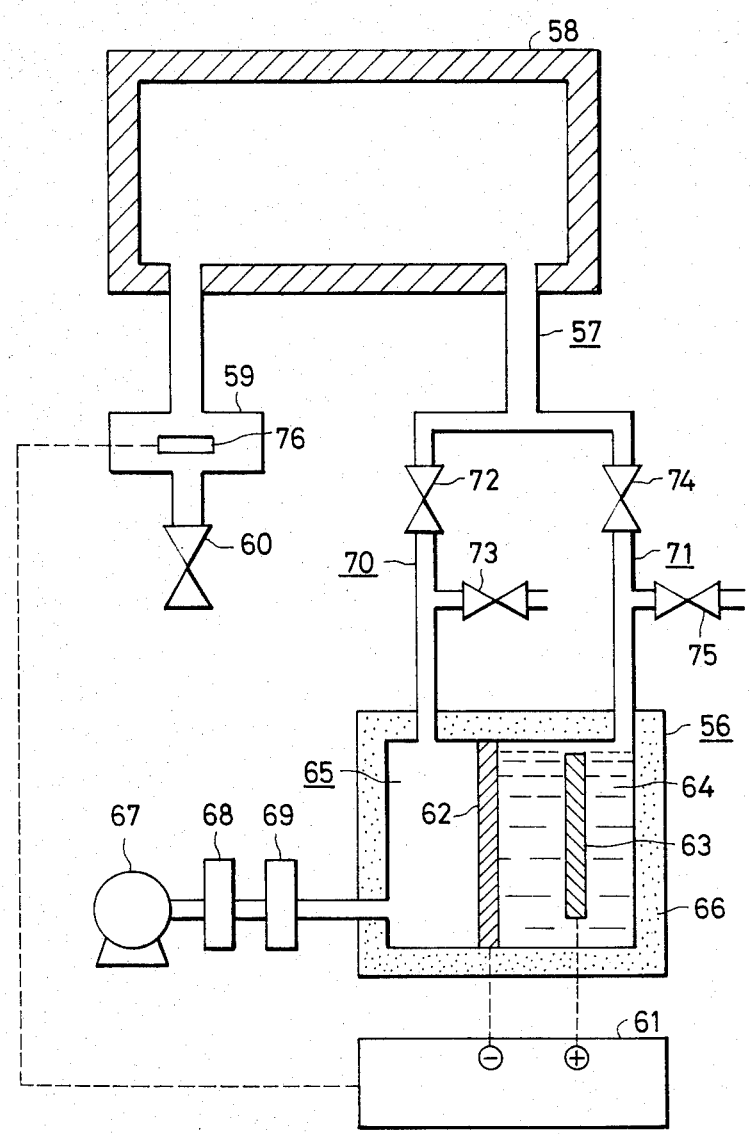

FIG. 3 is an explanatory diagram showing an oxygen concentration controlling system according to a third embodiment of the invention.

Roughly stated, the oxygen concentration controlling system comprises: an electrochemical cell 56; a gas supply path 57; a chamber 58; an oxygen concentration detecting chamber 59; a relief valve 60; and a power control section 61.

The electrochemical cell 56 includes: a cathode 62 which is a gas diffusion electrode effective in the electrolytic reduction of oxygen; an anode 63 serving as an oxygen generating electrode; an electrolyte 64 of sulfuric acid solution; a cathode gas chamber 65; and a cell frame 66.

The electrochemical cell 56 is provided with an air lead-in pump 67, an air flow control valve 68 and an air flow meter.

The gas supply path 57 consists of a deoxygenated gas supply path 70 and an oxygen supply path 71. A deoxygenated gas supply valve 72 and a deoxygenated residual gas purge valve 73 are provided in the deoxygenated gas supply path 70. An oxygen supply valve 74 and an oxygen purge valve 75 are provided in the oxygen supply path 71.

The oxygen concentration in the chamber is controlled as follows:

The oxygen concentration in the chamber 58 is detected by an oxygen sensor 76 accommodated in the oxygen concentration detecting chamber 59. When the oxygen concentration thus detected is much higher than a predetermined value, the deoxygenated gas supply valve 72, the oxygen purge valve 75 and the relief valve 60 are opened, and the oxygen supply valve 74 and the deoxygenated residual gas purge valve 73 are closed. Under this condition, the air lead-in pump 67 is driven so that, while referring to the air flow meter 69, the flow rate of air is controlled by the air flow control valve 68 to supply air into the cathode gas chamber 65, while a constant DC voltage is applied between the cathode 62 and the anode 63 from a power source in the power control section 61. As a result, a deoxygenation reaction occurs at the cathode 62, so that the deoxygenated gas is supplied through the deoxygenated gas supply valve 72 into the chamber 58 and the gas expelled from the chamber 58 is purged out of the system through the oxygen concentration detecting chamber 59 and the relief valve 60. On the other hand, oxygen generated at the anode is purged out of the system through the oxygen purge valve 75. Thus, the oxygen concentration in the chamber 58 is gradually decreased. When the oxygen concentration reaches the predetermined value, the application of current from the power control section 61 is suspended, so that the pump 67 is stopped, and the deoxygenated gas supply valve 72 and the relief valve 60 are closed.

When the oxygen concentration in the chamber 58 is much lower than the predetermined value, the deoxygenated residual gas purge valve 73 and the relief valve 60 are opened, and the deoxygenated gas supply valve 72 and the oxygen purge valve 75 are closed. Under this condition, the air lead-in pump 67 is operated to supply ambient air into the cathode gas chamber 65 while a constant DC current is applied between the cathode 62 and the anode 63. As a result, oxygen generated at the anode 63 is supplied through the oxygen supply valve 74 into the chamber 58, while the gas expelled from the chamber 58 is purged out of the system through the oxygen concentration detecting chamber 59 and the relief valve 60. On the other hand, the residual gas deoxygenated at the cathode 62 is purged out of the system through the deoxygenated residual gas purge valve 73. Thus, the oxygen concentration in the chamber 58 is gradually increased to the predetermined value.

Fourth Embodiment

Figure 4:
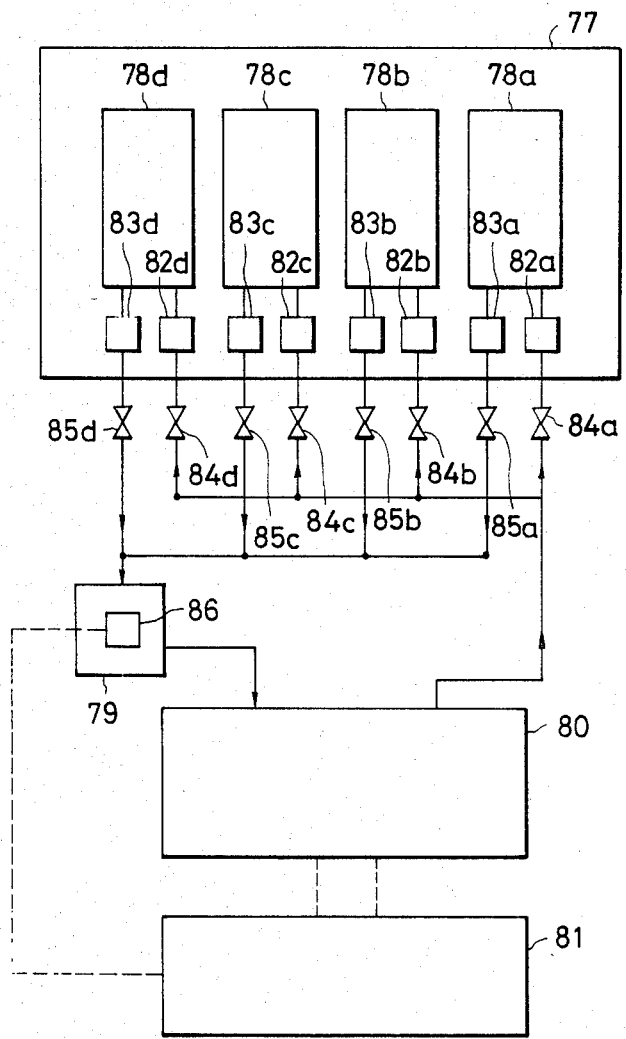

FIG. 4 is an explanatory diagram showing an oxygen concentration controlling system according to a fourth embodiment of the invention.

The system comprises: a chamber 77; small boxes 78a, 78b, 78c and 78d in the chamber 77; an oxygen concentration detecting chamber 79; an electrochemical cell 80 having both an oxygen removing function and an oxygen generating function; and a power control section 81. The small boxes 78a through 78d are coupled to the electrochemical cell 80 through pipes in which detachable supply path fluid couplings 82a, 82b, 82c and 82d, return path fluid couplings 83a, 83b, 83c and 83d, supply path valves 84a, 84b, 84c and 84d, and return path valves 85a, 85b, 85c and 85d are provided as shown in FIG. 4.

An oxygen sensor 86 is accommodated in the oxygen concentration detection chamber 79.

In the oxygen concentration controlling system thus configured, the oxygen concentration of any selected small box may be individually controlled with the respective supply path valve and return path valve opened.

Any small box can be taken out of the chamber 77 after its fluid couplings have been disconnected.

The oxygen removing capacity and oxygen generating capacity of the electrochemical cell 80 can be small enough to correspond to the internal volume of each small box instead of that of the chamber 77.

Fifth Embodiment

In the case where a cation exchange membrane is used as an electrolyte, the cation exchange membrane—electrode junction is fabricated as follows:

First, 50 cc of water is added to 100 g of 200-mesh iridium oxide powder, and then a polytetrafluoroethylene dispersion including 60% solid is added thereto. The mixture is sufficiently agitated. Thereafter, 30 cc of acetone is added to the mixture to prepare a muddy mixture. The muddy mixture is rolled into a sheet of iridium oxide by a roll press. The sheet of iridium oxide is placed on one side of a cation exchange membrane ("Nafion" made by DuPont Co.) which is obtained by applying sulfonic acid radical to perfluorocarbon, and is then pressed under a pressure of 100 kg/cm² at a temperature of 100° C.

On the other hand, 50 g of 200-mesh platinum black powder and 50 g of 400-mesh cation exchange resin powder prepared by adding sulfonic acid radical to stylene-divinyl benzene copolymer are sufficiently mixed together. Then, 50 cc of water is added to the mixture, and 60% polytetrafluoroethylene dispersion is added thereto. The resultant mixture is sufficiently agitated. Thereafter, 30 cc of acetone is added to the mixture to obtain a muddy mixture.

The muddy mixture is rolled into a sheet. The sheet thus obtained is placed on the other side of the cation exchange membrane, on the one side of which the sheet of iridium oxide has been placed as described above, and is then pressed under a pressure of 300 kg/cm² at a temperature of 100° C.

Thus, the cation exchange membrane - electrode junction is fabricated. The iridium oxide layer serves as the oxygen generating anode, and the layer of platinum and cation exchange resin powder mixture serves as the oxygen reduction cathode.

In each of the above-described embodiments, only one electrochemical cell is employed; however, it goes without saying that a plurality of electrochemical cells can be employed in the system.

What is claimed is:

1. An oxygen concentration controlling method, comprising:

providing an electrochemical cell having a cathode comprising a gas diffusion electrode, an anode comprising an oxygen generating electrode, an electrolyte, a cathode gas chamber and an oxygen lead-out section, and having both a deoxygenating function and an oxygen generating function and coupling said cell to a chamber, the oxygen concentration in which is to be controlled, in such a manner that a deoxygenating path including said cathode gas chamber and an oxygen supplying path including said oxygen lead-out section are formed, attaching a deoxygenated residual gas purge valve to said deoxygenating path, and disposing an oxygen purge valve in said oxygen supplying path, detecting the oxygen concentration in one of said chamber and said deoxygenating path by means of an oxygen sensor, and when the oxygen concentration is much higher than a predetermined value: opening a deoxygenating path valve in said deoxygenating path and said oxygen purge valve, closing an oxygen supplying path valve in said oxygen supplying path and said deoxygenated residual gas purge valve, applying a DC voltage between said cathode and said anode in said electrochemical cell to cause a deoxygenation reaction at said cathode, supplying a deoxygenated gas produced by said deoxygenation reaction through said deoxygenating path into said chamber, and purging oxygen generated from said anode through said oxygen purge valve, so that the oxygen concentration in said chamber is decreased to said predetermined valve, and when the oxygen concentration is much lower than said predetermined value: opening said oxygen supplying path valve in said oxygen supplying path and said deoxygenated residual gas purge valve, closing said deoxygenating path valve in said deoxygenating path and said oxygen purge valve, supplying ambient air into said cathode gas chamber while applying a DC voltage between said cathode and said anode in said electrochemical cell to cause an oxygen generating reaction at said anode, supplying the oxygen generated thereby through said oxygen supplying path into said chamber, and purging deoxygenated residual gas produced at said cathode through said deoxygenated residual gas purge valve, so that the oxygen concentration in said chamber is increased to said predetermined value.

2. A method as claimed in claim 1, wherein said deoxygenating path is of a circulation type, so that gas purged from said chamber is supplied to said cathode gas chamber by a circulating pump.

3. A method as claimed in claim 1, in which, when the oxygen concentration in said chamber is much higher than said predetermined value, an air lead-in pump supplies ambient air into said cathode gas chamber, and deoxygenated air provided by said deoxygenation reaction at said cathode is supplied into said chamber.

4. A method as claimed in claim 3, and further including preventing an increase in the pressure in said chamber otherwise caused by supplying deoxygenated gas or oxygen gas thereinto by purging said gas through a relief valve connected to said chamber.

5. An oxygen concentration controlling system, comprising:
- an electrochemical cell having a cathode comprising a gas diffusion electrode, an anode comprising an oxygen generating electrode, an electrolyte, a cathode gas chamber and an oxygen lead-out section, and having both a deoxygenating function and an oxygen generating function;
- a chamber, the oxygen concentration in which is to be controlled;
- a deoxygentating path extending between said cathode gas chamber and said chamber;
- an oxygen supplying path extending between said chamber and said oxygen lead-out section;
- a power control section; and
- an oxygen sensor provided in one of said chamber and said deoxygenating path.

6. A system as claimed in claim 5, in which said electrolyte is one of a potassium hydroxide and a sodium hydroxide solution.

7. A system as claimed in claim 5, in which said electrolyte is a sulfuric acid solution.

8. A system as claimed in claim 5, in which said electrolyte is a cation exchange membrane prepared by applying sulfonic acid radical to perfluorocarbon.

9. A system as claimed in claim 5, in which said electrolyte is a cation exchange member prepared by applying sulfonic acid radical to perfluorocarbon, and said cathode comprises a mixture of a platinum group metal powder, cation exchange resin powder and a fluorocarbon resin, said cathode being bonded to said cation exchange membrane.

10. A system as claimed in claim 5, in which said deoxygenating path and oxygen supplying path or a common path to which said deoxygenating path and oxygen supplying path are coupled are connected directly to said chamber.

11. A system as claimed in claim 5, in which said deoxygenating path and said oxygen supplying path are connected to said chamber via detachable fluid couplings.

12. A system as claimed in claim 5, in which said chamber comprises a plurality of small individually controlled subchambers connected to a common path to which said deoxygenating path and oxygen supplying path are coupled.

13. A system as claimed in claim 5, further including valves disposed in said respective paths for coupling or decoupling communication between said cathode gas chamber and said chamber, and between said oxygen lead-out section and said chamber.

14. A system as claimed in claim 5, further including overpressure release and underpressure compensating valves coupled to said chamber for preventing a substantial overpressure or underpressure in said chamber.

15. A system as claimed in claim 13, further including purge valves connected to said deoxygenating and oxygen supplying paths for respectively purging a deoxygenated residual gas and oxygen gas when opened.

16. A system as claimed in claim 11, wherein at least a portion of said deoxygenating and oxygen supplying paths are in common.

* * * * *